United States Patent
Frager et al.

(10) Patent No.: US 6,776,979 B2
(45) Date of Patent: Aug. 17, 2004

(54) PERIODONTAL TREATMENT COMPOUND AND METHOD OF USE

(76) Inventors: Marvin B. Frager, 210 Terramar, San Clemente, CA (US) 92673; R. Douglas Gaynor, 28048 Paseo Hacienda, San Juan Capistrano, CA (US) 92675; John R. Taylor, 801 N. La Reina St., Anaheim, CA (US) 92801

( * ) Notice: Subject to any disclaimer, the term of this patent is extended or adjusted under 35 U.S.C. 154(b) by 2 days.

(21) Appl. No.: 10/334,373

(22) Filed: Dec. 30, 2002

(65) Prior Publication Data

US 2004/0126440 A1 Jul. 1, 2004

(51) Int. Cl.[7] .......................... A61K 7/28; A61K 38/46; A61K 33/34; A61K 31/715; A01N 63/00
(52) U.S. Cl. ............................. 424/50; 424/53; 424/57; 424/58; 424/93.45; 424/94.6; 424/630; 424/643; 514/54; 514/474
(58) Field of Search ............................. 424/50, 53, 57, 424/58, 93.45, 94.6, 630, 643; 514/54, 474

(56) References Cited

U.S. PATENT DOCUMENTS

| | | | |
|---|---|---|---|
| 5,472,684 A | * 12/1995 | Nabi et al. ................... 424/49 |
| 5,683,678 A | * 11/1997 | Heckert et al. ............... 424/52 |
| 5,804,165 A | 9/1998 | Arnold ......................... 424/44 |
| 5,817,294 A | 10/1998 | Arnold ......................... 424/44 |
| 5,908,613 A | * 6/1999 | Bozzacco .................... 424/50 |
| 6,086,854 A | 7/2000 | Arnold ......................... 424/44 |
| 2003/0129260 A1 | * 7/2003 | Watson et al. .............. 424/732 |
| 2003/0203054 A1 | * 10/2003 | Selzer et al. ................ 424/732 |

* cited by examiner

Primary Examiner—Raymond J. Henley, III
(74) Attorney, Agent, or Firm—Frank G. Morkunas

(57) ABSTRACT

An oral compound of water; glycerin; a cranberry source; methylsulfonylmethane; melaleuca alternifolia oil; hydroxyethylcellulose; and a surfactant, in proper combination for use by injecting the compound around a person's gum line followed by its use in a dental tray over a person's teeth and gums for a specified period of time.

The next phase to the overall treatment regimen is a daily health care regimen involving:

a systemic immune defense compound having colostrum beta 1,3 Glucans; fructo-oligosaccharides; amla fruit 4:1; inositol hexaphosphate; selected minerals; selected enzymes; selected probiotics; and methylsulfonylmethane;

an antimicrobial compound having sodium bicarbonate, silicone dioxide, and a cranberry source; and an oral probiotic compound having selected probiotics; vitamin C; and colostrum.

32 Claims, No Drawings

PERIODONTAL TREATMENT COMPOUND AND METHOD OF USE

CROSS REFERENCES TO RELATED APPLICATIONS

None

STATEMENT REGARDING FEDERALLY-SPONSORED RESEARCH OR DEVELOPMENT

None

BACKGROUND OF THE INVENTION

This present invention relates to an improvement in office hygiene treatment and follow-up care, and more particularly to treatment and prevention of periodontal disease.

The gums of one's mouth and the bone under the gums and around the teeth hold one's teeth firmly in place. Periodontal disease is an infection of that gum. Its manifestations include an increase in gingival sulcus [pocket or furrow] depth, inflamed gingival tissues, bleeding gums, loss of bone structure, bad breath and increase of plaque, calculus and harmful bacteria in the periodontal sulcus. The sulcus is the depth of the space below the visible crest of gingiva of the lower teeth and above the visible crest of the gingiva of the upper teeth and the actual location of the gingival attachment to the tooth. Sulcus depths of 1 mm to 3 mm are considered normal, 4 mm and over are considered unhealthy and disease involved. Periodontal disease is commonly referred to as gum disease and is caused by the build-up and retention of dental plaque (i.e., a sticky mass of harmful germs [bacteria]) in the space between the gum and tooth. It is estimated that there are about 300 different types of bacteria in one's mouth. Of this amount, dental scientists have found that about a dozen of these nearly 300 bacteria can lead to and cause gum diseases. As it is presently understood, however, not all bacteria are harmful. In fact, many are helpful. As a result, not all bacteria should be eliminated, only the harmful bacteria which cause or contribute to periodontal disease.

It is also estimated that there are approximately 200 million people in the United States alone that are affected by some form of periodontal disease. In the 1960's the cause and treatment of periodontal disease was not well understood. It was then commonly believed that deep cleaning and some form of surgery, either curettage of the lining of the sulcus gum tissue, or surgical removal of the infected tissue was the treatment of professional choice. This was costly, painful and cumbersome for doctor and patient alike, and was not a permanent cure. The problem could recur and the same treatment would resume followed by the same temporary results. Further research later demonstrated that periodontal disease was more related to the build-up of plaque and bacteria in the gum space as well as poor periodontal and systemic immunity. This build-up caused the gum attachment to gradually pull away from the tooth leaving a pocket or furrow (sulcus) into which more plaque and bacteria could flourish. The greater the build-up, the greater the separation, the more severe the problem.

In the early 90's, based on these and other findings, more attention was given to the removal of this built-up plaque and bacteria, typically by the use of chemical agents or oral antibiotics or both. Lasers became a popular source for removing the tissue lining infected with plaque and bacteria. These procedures, though fine for removal of the plaque and bacteria, did nothing to prevent a recurrence. Whatever habits the patient had or whatever one's immunity, a recurrence was most probable. Nothing in the prior art treatment regimens provided for a simple, user-friendly preventive oral health regimen to attack the problems associated with periodontal disease at their incipient stages, or before, or after.

More and more attention is now being given to attacking the harmful bacteria, which are now well recognized as the main contributors to periodontal disease. Treatment protocols presently include antibiotic gels applied by syringe into the infected gum space, chemical rinses, time-released antibiotic chips inserted into the infected gum space, chemical flushes into the infected gum space, and stronger oral antibiotics.

These invasive chemical and antibiotic approaches are having some success in the treatment of periodontal disease, thereby decreasing the amount of periodontal procedures such as curettage and surgery. However, the overall satisfaction of both doctor and patient is still less than optimum and less than desired. Repeated use or over-use of antibiotics can compromise the immune system of the patient. Though these antibiotic approaches do help the periodontal tissues they also are inherent with problems and other undesirable side effects. They mask the real problem by treating the symptoms not the cause of the problem; they are expensive, they are not user-friendly, and they lack a comprehensive approach to the treatment of the whole mouth.

In July of 1998, the American Academy of Periodontology launched an effort to educate the public about new findings that support the proposition that infections in the mouth can wreak havoc elsewhere in the body. From these findings, many oral health-care professionals believe that persons with periodontal disease may be at greater risk of other and more serious health problems than those persons without the disease. Various other studies suggest, or an inference can be made to, a connection between periodontal disease and an increased risk for developing heart disease, suffering a stroke, developing uncontrolled diabetes, encountering pre-term births, and developing respiratory disease and other health problems.

Evidence continues to mount supporting these connections or links. While more research is required to definitively conclude that people with periodontal disease are at higher risk for developing heart disease, stroke, uncontrolled diabetes, pre-term births, and respiratory disease, periodontists do know that periodontal disease is a bacterial infection and can enter the blood stream, thereby providing the disease great access to all major organs. As such it is a cause for serious concern.

Several theories exist to explain the link between periodontal disease and heart disease. One theory is that oral bacteria can affect the heart when they enter the blood stream, attaching to fatty plaques in the coronary arteries (heart blood vessels) and contributing to clot formation. Coronary artery disease is characterized by a thickening of the walls of the coronary arteries due to the buildup of fatty proteins. Blood clots can obstruct normal blood flow, restricting the amount of nutrients and oxygen required for the heart to function properly. This may lead to heart attacks.

To develop an effective and efficient periodontal treatment program, the program must be based on a natural healing approach, which centers on the dental hygiene department of a dental office, rather than on a continued and repeated reliance and over-reliance, on antibiotics and chemicals. Many oral health-care professionals are aware of this and thus have attempted to create products or procedures to be used in the dental offices to combat this disease.

Many of the doctors and their patients are not satisfied with the current and past treatments and lack of long-term results. Because of cost and safety limitations, many current methods target treating only quadrants of the mouth, one at a time, per each office visit. If the entire mouth requires treatment, up to four office visits would generally be required. More office appointments result in greater expense, more time away from work, from home, and from family.

The cost of current treatments can range from approximately $200–$400 per treatment and these generally only target select quadrants of the mouth, one at a time. This can be rather expensive when more then one quadrant requires treatment, which generally is the case. The upshot from the costs involved and the time involved is that many patients in need of such treatment delay or, worse yet, decline treatment. When considering the estimates that nearly 200 million people in the United States [80% of all adults and teenagers] have some degree of gum disease, it is very important to create a treatment that most will feel they can afford to engage and, thereby, are more inclined to so engage.

Even with successful treatment of periodontal disease and care in the dental office, an overwhelming and demonstrated problem is follow-up self-care; i.e., systematic and regular brushing and flossing. Most people do not consistently engage in the practice of regular brushing and flossing necessary to preventive care and to post-treatment care. A great need would be satisfied by the creation of a method and product, designed with its ease and simplicity of use, safety of use, and affordability in mind. Such would increase home care oral treatment targeted to prevent periodontal disease but is lacking in the prior art.

There is, therefore, a need for treatments which are, at a minimum, more comprehensive in their initial approach; i.e., a full mouth disinfection [FMD] which can be performed and completed in one appointment thereby limiting time away from other endeavors and reducing costs significantly. The present invention has been created to fill the void. This coupled with easy-to-use and affordable continued home care would aid greatly in reducing recurrences of periodontal disease and minimize other health risks associated with periodontal disease.

Accordingly, several objects and advantages of the present invention are to:
 a. Provide a low-cost, effective, easy-to-use in-office treatment regimen for prevention of, and as an adjunct in treating, periodontal disease;
 b. Produce a non-intrusive in-office treatment regimen for prevention of and as an adjunct in treating periodontal disease;
 c. Create an in office treatment compound/gel for periodontal disease made up of natural components;
 d. Establish low-cost, effective, an easy-to-use in-home treatment regimen for periodontal disease;
 e. Prevent or greatly reduce recurrence of periodontal disease; and
 f. Provide a whole-body immunity treatment regimen.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims.

BRIEF SUMMARY OF THE INVENTION

The above-noted problems, among others, are overcome by the present invention. Briefly stated, the present invention contemplates an oral compound comprising distilled water; pure glycerin; a cranberry source, either cranberry extract or concentrated cranberry powder; methylsulfonylmethane; melaleuca alternifolia oil; hydroxyethylcellulose; and a surfactant, in combination for use by injecting the compound around a person's gum line followed by use of such compound in a tooth-and-gum tray over a person's teeth and gums.

The oral compound contains between about 15% to about 45% by weight or by volume or by concentration of water; between about 30% to about 70% by weight or by volume or by concentration of glycerin; between about 3% to about 8% by weight or by volume or by concentration of cranberry source; between about 5% to about 15% by weight or by volume or by concentration of methylsulfonylmethane; between about 1.5% to about 50% by weight or by volume or by concentration of melaleuca alternifolia oil; between about 1.5% to about 7% by weight or by volume or by concentration of hydroxyethylcellulose; and between about 0.05% to about 1.5% by weight or by volume or by concentration of surfactant.

The next phase to the overall treatment regimen is a daily health care [in-home] regimen involving:
 a. A systemic immune defense compound [SID] one or more times per day. The SID compound having colostrum [preferably bovine colostrum]; beta 1,3 Glucans; fructo-oligosaccharides; amla fruit 4:1; inositol hexaphosphate; minerals [preferably chelated calcium, zinc, and copper]; enzymes [preferably amylase, lipase, and cellulase]; a selection of probiotics [preferably bifidobacterium longum, lactobacillus plantarum bifidobacterium bifidum, lactobacillus casei, and lactobacillus acidophilus]; and methylsulfonylmethane;
 b. An antimicrobial compound at least once per day. The antimicrobial compound having sodium bicarbonate, silicone dioxide, and a cranberry source [such as cranberry extract or cranberry concentrate powder]; and
 c. An oral probiotic compound at least once per day. The oral probiotic compound including a selection of probiotics [preferably lactobacillus acidophilus, lactobacillus plantarum, lactobacillus salivarius, lactobacillus sporogenes, bifidobacterium longum]; vitamin C; and colostrum [preferably bovine colostrum].

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiments may be readily utilized as a basis for modifying or designing other structures, components, and elements and employing other methods for carrying out the same purposes of the present invention. It also should be realized by those skilled in the art that such equivalent constructions and methods do not depart from the spirit and scope of the inventions as set forth in the appended claims.

DETAILED DESCRIPTION OF THE INVENTION

The treatment compounds and in-office and in-home treatment protocols and regimens [i.e., daily health regimen, or as near to daily as possible or desired] and compounds envisioned by the present invention provide for more effective care, less intrusive in execution, and more permanent in nature than that set forth in the prior art discussions above.

The in-office treatment protocol is not limited to one section or quadrant per visit, but provides for a comprehensive full-mouth treatment and comprehensive full-mouth disinfectant for the patient during a single visit and, with continued in-home treatment [i.e., daily health regimen], provides for continued immune system support through and by the supplementation of healthy flora and other natural ingredients.

Though the compounds and regimens are illustrated for use on, for, and by human beings, the compounds of the present invention perform equally well for animals suffering from periodontal disease or any form of periodontal disease associated with their species. The treatment regimen and procedures may be appropriate for a particular species or may be modified to fit the particular needs and physical structure of the infected animal.

A typical in-office procedure starts with a periodontal examination and evaluation performed by an oral health-care professional. This generally consists of a periodontal depth analysis, which may be done before and after the treatments, and is comprised of measuring the sulcus depths around each tooth. There are six measurements taken around the circumference of each tooth with a calibrated straight instrument. Measurements of 4mm and over are considered unhealthy and diseased.

A bleeding analysis is done before and after the treatments and rated on a scale of 0–5, based on the amount of bleeding found during measuring of the sulcus depth. Zero ["0"] being no bleeding, 3 being moderate bleeding, 5 being severe and uncontrolled bleeding. Bleeding is indicative of some stage of periodontal involvement. A breath analysis is done based on the patient's perception of their oral odor before and after the treatments. The analysis is rated on a scale 0–5. Zero ["0"] is no odor, 3 is moderate odor, 5 is severe odor. Breath odor is a result of a harmful bacteria buildup in the sulcus and on the tongue. Breath odor is indicative of some stage of periodontal involvement as well as possible digestive problems.

Upon detecting a problem of periodontal disease, such will be fully explained to the patient along with the suggested treatment regimen, both in-office and in-home and its estimated cost. If the patient agrees to the treatment, the in-office phase begins. An impression of the patient's teeth [upper and lower] is first made. The purpose of taking an impression is to fashion a custom-fitted vacuum tray for later use. The tray should fit snugly over the patient's teeth, cover up to about 2–3 mm of gingival tissue [gums], and preferably form a snug seal therefor.

A routine teeth cleaning, as is conventionally performed by most current oral health-care professionals, is completed followed by the treatment method of the present invention or as soon as possible at the next visit. The first step of this process of the present invention is to introduce into the patient's mouth an antimicrobial compound comprised generally of a carbon dioxide [or equivalent source] such as, but not limited to, sodium bicarbonate [$NaHCO_3$]; silicone dioxide; and a sweetener such as but not limited to a cranberry source [cranberry extract or cranberry concentrate powder]. All of which are commercially available. In this regard, the sodium bicarbonate [$NaHCO_3$] was obtained from Arnold Labs, the silicone dioxide also from Arnold Labs, and the cranberry extract [or cranberry concentrate powder] from Decas Cranberry.

This antimicrobial compound preferably is in chewable tablet form, though it need not be, and is designed to combine and form a foaming action with the patient's saliva. The patient is instructed to chew and swish this combination within the patient's mouth for 10 to 240 seconds; depending on the compositions of the ingredients, 60 seconds of swishing is generally sufficient after which it may be discarded.

This antimicrobial compound may be in any form but, as set forth above, tablet-form seems the most suited for the intended purpose and ease of use. In the formulation, the cranberry component is at a range of about 1% to about 50% although about a 10% concentration does work well. The sodium bicarbonate [$NaHCO_3$] and silicon dioxide components should be approximately in equal parts and may range from about 25% to about 80% for each, although about a 45% concentration does work well. The percent ranges set forth above may be by weight or by volume or by concentration.

The antimicrobial compound is designed to adhere to the gums and the teeth for several hours. The purpose of this antimicrobial compound is to kill bacteria within the mouth, provide a clean environment in the mouth to better accept and utilize the rinse and treatment compound later to follow, and to thereby aid in the overall healing process of the infected periodontal tissues.

The next step is for the patient to rinse the mouth, with a novel rinse formulation, from between 10–240 seconds; generally 60 seconds will suffice for the intended result. The rinse compound used is a unique chlorine dioxide formulation [or sodium chlorite formulation], crafted to further reduce the bacteria count in the patient's mouth, to neutralize the effects of the sodium bicarbonate from the antimicrobial compound, and to debride the teeth and gums to an extent that the teeth and gums so debrided will better accept and utilize to the fullest the treatment compound to follow. This rinse compound is comprised of between about 80.0% to about 99.0% water [preferably distilled water) and between about 1.0% to about 20.0% chlorine dioxide [or equivalent amounts of sodium chlorite]. The percent ranges set forth above, and below, may be by weight or by volume or by concentration.

These ranges are suitable for the intended purpose but better results are realized with a range of about 95.0% to about 98.5% water and between about 5.0% to about 1.5% chlorine dioxide [or sodium chlorite]. Better results have been realized with a formulation of about 97.5% water and about 2.5% chlorine dioxide [or sodium chlorite]. These elements are commercially available. In this regard, the water and chlorine dioxide [or sodium chlorite] used for this formulation was obtained from Arnold Labs; though any similar water and chlorine dioxide or sodium chlorite may be used.

After the rinse has been applied, the treatment compound/gel is next administered. If the periodontal disease is severe and had greatly affected the gums, the treatment compound/gel is loaded into a syringe and the oral health-care professional injects the treatment compound/gel into the deeper periodontal lesions. This may be followed by applying the treatment compound/gel in the syringe around the entire gum line of the patient's mouth. This ensures the fullest coverage of the treatment compound after the trays are later applied. Last, the treatment compound/gel is applied into the trays and the trays inserted over the upper and low teeth and gums. The trays, with treatment compound/gel, fully seat over all of the patient's teeth and over the gums between about 2–3 mm. This ensures good coverage by the treatment compound/gel of all of the infected areas.

If the severity of the periodontal disease is not too great, typically the last step may be the only step in this process after the rinse step described above. For best and most thorough results, it is best to follow all the steps enumerated above after the rinse; i.e., injection into the deeper periodontal lesions, application over the gum line and teeth, and application of the compound/gel filled trays over the teeth and gums. The trays are left in the patient's mouth from approximately 5 minutes to about 30 minutes depending on the severity or lack thereof, of the periodontal disease. In most cases, approximately 10 minutes will suffice.

The dental-care professional then removes the trays from the patient's mouth, inspects the teeth and gums, and inspects the trays. The patient should then rinse with water or any other suitable solution. It is then best that the patient take the oral probiotic compound [as described in detail later], allow it to mix with one's saliva [oral probiotic mixture], and to swish it around within the mouth for between about 10 seconds to about 240 seconds; swishing for about 60 seconds, however, will generally suffice for the intended purpose. For best results, after swishing, the mixture should be swallowed.

The patient is then released with an in-home/daily health care regimen to maintain dental health and to eliminate recurrence of periodontal disease or, at a minimum,-to reduce the chance of recurrence of periodontal disease. If the severity of the patient's periodontal disease is extensive, the patient is requested to return for additional in-office treatments as described above.

To attain and maintain the best dental health possible, the patient should return to the dental office at least 2–4 times per year, or at a minimum, at least 2 times per year. At each of these follow-up regular in-office visits, the procedures described above should be followed. For best and most thorough results, it is best to follow all the steps enumerated above after the rinse; i.e., injection into the deeper periodontal lesions, application over the gum line, and application of the gel-filled trays over the teeth and gums. The trays are left in the patient's mouth from approximately 10 minutes. In most cases, approximately 10 minutes will suffice.

The treatment compound of the present invention comprises a formulation of water [preferably distilled water], concentrated glycerin [approximately 99.9% pure-kosher] cranberry concentrate powder or cranberry extract [approximately 90% pure], methylsulfonylmethane [approximately 99.995% pure], melaleuca alternifolia oil [commonly referred to as "Australian tea-tree oil" and shall be referred to hereinafter as 'tea-tree oil'], hydroxyethylcellulose, and a suitable surfactant. Typical compounds for a suitable surfactant include, but not limited to, polysorbate 60, sodium cocamide betaine, or Sodium Lauryl Sulfate; all available from Arnold Labs. The water, glycerin, and hydroxyethylcellulose, addressed above, are also available from Arnold Labs. The cranberry concentrate powder is available from Decas Cranberry; the methylsulfonylmethane from Carolwood Corporation; and the tea-tree oil from Arista Industries, Inc. The vendors of the compounds are not the only vendors from which these compounds may be obtained and mention of them herein is for illustration purposes only, not by way of limitation. Any similar or equivalent compound bearing equivalent properties will suffice. Through extensive research and experimentation, the compounds listed above have been found best suited to the treatment of periodontal disease as described herein.

Each component above is commonly available but must be mixed to proper ratios for the treatment compound to be most effective. The percent ranges set forth below for these components may be by weight or by volume or by concentration. In this regard, the treatment compound provides good results in the treatment of periodontal disease if it contains between about 15% to about 45% water; between about 30% to about 70% glycerin; between about 3% to about 8% cranberry concentrate powder; between about 5% to about 15% methylsulfonylmethane; between about 0.05% to about 1.5% surfactant; between about 1.5% to about 50% tea-tree oil; and between about 1.5% to about 7% hydroxyethylcellulose. Best results have been realized when the treatment compound contains approximately 26% water; approximately 50% glycerin. [with about 50.8% being optimum]; approximately 4.65% cranberry concentrate powder; approximately 10.6% methylsulfonylmethane; approximately 0.07% surfactant; between approximately 3–5% tea-tree oil [with approximately 4.3% being optimum]; and approximately 4.3% hydroxyethylcellulose. The percentage ranges herein may be by weight or by volume.

This in-office treatment ensures the most effective treatment for periodontal disease. It should be continued on a routine basis several times per year depending of the severity of the periodontal disease, the patient's in-home regimen, the patient's habits, and the patient's health history. In most cases, two times per year will suffice; in more severe cases, four to six times per year may be required [less if the patient faithfully administers the prescribed in-home care].

The in-home daily health care should entail regular brushing of the teeth [after every meal, whether the meal is eaten at home or elsewhere, and before retiring for the evening], should entail daily flossing, and should entail tending to one's overall immune defense system. It must be understood that any one or all or any combination of the above, in any degree, will facilitate better dental health. Performing all to the maximum extent will reward the patient with excellent dental health and improved overall health.

The in-office treatment regimen and compounds associated therewith have been applied in a clinical setting encompassing 41 patients covering a period of two months per patient. The overall time to perform the entire study was approximately 10 months. There were 20 control patients and each received a cleaning and four quadrants of deep cleanings and root planings. There were 21 test patients and each received a cleaning and four quadrants of deep cleanings and root planings. The test patients also received three in office gel treatments and two months of home care products.

All patients had periodontal disease, which ranged from type 1 gingivitis (mild disease) to type 3 (moderate) to type 5 (severe/advanced). Of the 21 test patients:

a. One have type 1;

b. Eight had type 2;

c. Nine had type 3;

d. Two had type 4; and e. One had type 5.

The results of this treatment regimen reflect a 66.4% reduction in the number of pocket sizes which were 4 mm or greater at the start of treatment to a pocket of less than 4 mm after treatment [these pockets also decreased in overall size by an average of 25.6%]; a 15.1% reduction of the overall average sulcus depth; a 54.7% reduction in bleeding of the gums; and an 80.2% reduction in perceived unpleasant breath odor by the patient. Other favorable aspects to the regimen and compounds use include the time it took to complete the treatment, acceptability of the tastes of the various compounds, and no discomfort from use of the compounds or the regimen applied.

The in-home treatment [daily health care regimen] briefly mentioned above entails, at most, a daily three component method for maintaining superior periodontal health. The components of the method are as follows:

a. A systemic immune defense [SID] compound to be administered at least twice a day;

b. A antimicrobial compound [the same compound described for the in-office treatment] administered at least three times per days [after eating or after brushing or any combination thereof]; and c. An oral probiotic compound administered once per day [generally prior to retiring for the evening to thereby maximize its effects].

The systemic immune defense [SID] compound is generally comprised of:

a. immune system support nutrients comprising colostrum [preferably bovine colostrum], Beta 1,3 Glucans, and fructo-oligosaccharides [or inulin];

b. amla fruit 4:1;

c. inositol hexaphosphate;

d. minerals comprising calcium, zinc, and copper [all preferably in the chelated form];

e. enzymes comprising amylase, lipase, and cellulase;

f. probiotics comprising bifidobacterium longum, lactobacillus plantarum bifidobacterium bifidum, lactobacillus casei, and lactobacillus acidophilus; and g. methylsulfonylmethane [MSM].

This SID compound, after ingestion, systemically addresses the issues of oral health while balancing the delicate ecology of the entire gastro-intestinal tract. This systemic approach is considered to be the best approach in this regard to getting to the root of the problem in counteracting (through ecological balance) the bacteria associated with periodontal disease. The role of the SID compound in the home care method is that of providing a foundational, holistic approach to superior periodontal health. The ingredients are all natural. The formulation should be administered at least daily, once in the morning and once in the evening.

The SID compound may be in any form though a capsule form is preferred. For illustration purposes only, not by way of limitation, based on a capsule of 750 milligrams, the elements of the systemic immune defense compound may be comprised of:

a. approximately 50 mg to about 500 mg of the bovine colostrums will function or react adequately. Approximately 225 milligrams per capsule is preferred. The product used for this formulation was obtained from the National Enzyme Company in Forsyth, Mo.

b. approximately 10 milligrams per capsule to about 200 milligrams per capsule of beta 1,3 glucans will function or react adequately. Approximately 75 milligrams per capsule concentration is preferred. The product used for this formulation was obtained from the National Enzyme Company.

c. approximately 2 milligrams per capsule to about 150 milligrams per capsule of fructo-oligosaccharides will function or react adequately. Approximately 25 milligrams per capsule concentration, however, is preferred. The product used for this formulation was obtained from the National Enzyme Company.

d. approximately 10 milligrams per capsule to 300 milligrams per capsule of amla fruit 4:1 extract will function or react adequately. Approximately 100 milligrams per capsule is preferred. The product used for this formulation was obtained from the National Enzyme Company.

e. approximately 1 milligram per capsule to about 50 milligrams per capsule of inositol hexaphosphate will function or react adequately. Approximately 2.5 milligrams per capsule concentration is preferred. The product used for this formulation was obtained from the National Enzyme Company.

f. minerals:

(1) the quantity of zinc chelate ranges from approximately 2 milligrams per capsule to about 75 milligrams per capsule. Approximately 7.5 milligrams per capsule concentration is preferred.

(2) the quantity of chelated copper ranges from approximately 50 micrograms per capsule to about 2 milligrams per capsule. Approximately 1 milligram per capsule concentration is preferred.

(3) the chelated calcium ranges from approximately 5 milligrams per capsule to about 150 milligrams per capsule. Approximately 20 milligrams per capsule concentration is preferred.

The minerals used for this formulation were obtained from Albion Laboratories, Inc., of Clearfield, Utah. It is best that the minerals be in chelated form and also best that the minerals have a true molecular chelate. Albion Laboratories, Inc., consistently produces the minerals of choice bearing a true molecular chelate which best serves the formulation and intended result for the SID compound.

g. enzymes; the enzyme blend of amylase, lipase, and cellulase are approximately of equal parts. For good effectiveness, the combination blend ranges from approximately 5 milligrams per capsule to about 50 milligrams per capsule Approximately 21 milligrams of each per capsule concentration is preferred. The products used for this formulation was obtained from the National Enzyme Company.

h. probiotics consisting of bifidobacterium longum, lactobacillus plantarum, bifidobacterium bifidum, lactobacillus casei, lactobacillus acidophilus should have a combined total of between about 100,000 to 6,000,000,000 colony forming units [cfu's] in equal parts. Approximately 1,250,000,000 cfu concentration is preferred [about 250,000,000 cfu for each of the five probiotic elements identified above]. The product species used for this formulation was obtained from Nebraska Cultures, Inc.

I. methylsulfonylmethane [MSM] should generally range from about 10 milligrams per capsule to about 300 milligrams per capsule. Approximately 100 milligrams per capsule concentration is preferred. The product used for this formulation was obtained from Carolwood Corporation.

The antimicrobial compound is comprised of primarily sodium bicarbonate, silicone dioxide, and cranberry concentrate powder for cranberry extract] as described earlier for the in-office treatment. Its part in the home care method is to kill off the harmful bacteria located in the oral cavity, and to prevent future adherence of these bacteria-types to the gums. It should be taken at least three times per day. The compound should be left within the mouth, chewed and swished for at least 10 to 240 seconds [60 seconds may be sufficient for optimal results depending on the patient's periodontal condition] after which the compound may be swallowed or discarded. Regardless, after swishing the patient should not rinse, eat, or drink anything for between about 30 to 90 minutes after administration of this compound. Not rinsing, eating, or drinking anything for about 60minutes after administration of this compound is preferred for maximum results.

The oral-probiotic compound is comprised primarily of probiotics (including lactobacillus acidophilus, lactobacillus plantarum, lactobacillus salivarius, lactobacillus sporogenes, bifidobacterium longum); vitamin C; and colostrum [preferably bovine colostrum]—all of which are commercially available. The role of this compound in the home care method is to re-populate the oral cavity with healthful bacteria; this is done with the objective of maintaining an ecological balance conducive to superior periodontal health. The oral-probiotic compound is to be administered last thing in the evening and should be chewed and swished in the mouth for at least 10 to 240 seconds [60 seconds, however, will suffice for the intended results depending on the patient's periodontal condition]. After this time period, the oral probiotic compound should be swallowed. The patient should not rinse, eat, or drink anything for the remainder of the evening after administration of this compound; or at a very minium, for at least four hours.

This oral probiotic compound may be in any form though a tablet form is preferred. For illustration purposes only, not by way of limitation, based on a capsule of 500 milligrams, the elements of the oral probiotic compound may be comprised of:

a. a probiotic blend of probiotic species comprising lactobacillus acidophilus, lactobacillus plantarum, lactobacillus salivarius, lactobacillus sporogenes, and bifidobacterium longum. The blend should contain approximate equal parts of each of the species. The cfu of the probiotic blend should range from approximately 100,000 cfu's to about 6,000,000,000 cfu's per tablet [from approximately 20,000 cfu's for each species to about 1,200,000,000 cfu's for each species]. Approximately 2,000,000,000 cfu's per tablet [approximately 500,000,000 cfu's for each species], however, is preferred. The product species used for this formulation was obtained from Nebraska Cultures, Inc., of Walnut Creek, Calif.

b. vitamin C should range from about 75 mg to about 500 mg; however 200 mg is preferred. The product used for this formulation was obtained from Nebraska Cultures, Inc.

c. colostrum [preferably bovine colostrum] ranging from approximately 50 milligrams per capsule to about 500 milligrams per capsule. Approximately 250 milligrams per capsule is preferred. The product used for this formulation was also obtained from Nebraska Cultures, Inc.

d. a suitable carrier may be combined with the above for ease of administration. Such carrier may be, but is not limited to, any liquid [water for example] combined or mixed with the above-listed elements which then is taken into one's mouth and chewed or swished within the mouth or both. The above-listed elements may be in powder form, in capsule form, in liquid form, or in tablet form. Experience has proven that the tablet form is most user friendly using as a carrier any commercially available compound to contain and hold the above-listed elements, plus a flavor or sweetening enhancer, is best.

Based on the 1500 mg tablet as an illustration, not by means of limitation, a suitable carrier may be, but is not limited to, a combination of maltodextrin, silicone dioxide, vegetable magnesium stearate, vegetable stearic acid, natural fruit flavoring [strawberry, raspberry, cranberry, cherry, and the like], natural vegetable coloring [beet root color for example], sorbitol, and stevia extract, or equivalents to any of the above and in any combination to comprise a 1500 mg tablet.

The in-office regimen and compounds associated therewith [i.e., antimicrobial compound, rinse compound, and the treatment compound described above] address and facilitate both the eradication of harmful bacteria and assist in continued immune system support. Adding the in-home health care regimen more comprehensively facilitates the above beneficial results through the supplementation of healthy flora and other natural immune supporting ingredients on a regular basis.

The present disclosure includes that contained in the present claims as well as that of the foregoing description. Although this invention has been described in its preferred form with a certain degree of particularity, it is understood that the present disclosure of the preferred form has been made only by way of example and numerous changes in the details of construction and combination and arrangement of parts and method steps may be resorted to without departing from the spirit and scope of the invention. Accordingly, the scope of the invention should be determined not by the embodiment[s] illustrated, but by the appended claims and their legal equivalents.

The invention claimed is:

1. A method of treating gum tissue comprising the steps of:
   (a) providing an oral compound comprising a mixture of water, glycerin, a cranberry source, methysulonylmethane, melaleuca alternifolia oil, hydroxyethylcellulose, and a pharmaceutically acceptable surfactant; and
   (b) applying said oral compound onto said gum tissue by injecting said oral compound around said gum tissue, between teeth and gum, and into pockets of said gum tissue.

2. A method of treating gum tissue comprising the steps of:
   (a) providing an oral compound comprising a mixture of water, glycerin, a cranberry source, methysulonylmethane, melaleuca alternifolia oil, hydroxyethylcellulose, and a pharmaceutically acceptable surfactant; and
   (b) applying said oral compound onto said gum tissue by providing a tooth-and-gum tray adapted to cover a patient's teeth and overlap said patient's gum line, placing said oral compound into said tooth-and-gum tray; and inserting said tooth-and-gum tray over said patient's teeth.

3. The method of claim 2 further comprising the step of maintaining said tooth-and-gum tray in place over said patient's teeth for between about 5 minutes to about 30 minutes.

4. A method of treating gum tissue comprising the steps of:
   (a) providing an oral compound comprising a mixture of water, glycerin, a cranberry source, methysulonylmethane, melaleuca alternifolia oil, hydroxyethylcellulose, and a pharmaceutically acceptable surfactant;
   (b) applying said oral compound onto said gum tissue; and
   (c) administering an antimicrobial compound prior to applying said oral compound onto said gum tissue, said antimicrobial compound comprising primarily a carbon dioxide source and silicone dioxide.

5. The method of claim 4 wherein said administering of said antimicrobial compound comprises the step of placing said antimicrobial compound in one's mouth, mixing one's saliva with said antimicrobial compound resulting in a antimicrobial-mixture, and swishing said antimicrobial-mixture within one's mouth for between about 10 to 240 seconds.

6. The method of claim 5 further comprising the step of administering a rinse compound either prior to or after administering said antimicrobial compound, said rinse compound comprising water and a chlorine source.

7. The method of claim 6 wherein said rinse compound is comprised of between about 80.0% to about 99.0% by volume of said water and between about 1.0% to about 20.0% by volume of said chlorine source, wherein said chlorine source is selected from the group consisting of chlorine dioxide and sodium chlorite.

8. A method of treating gum tissue comprising the steps of:
   (a) providing an oral compound comprising a mixture of water, glycerin, a cranberry source, methysulonylmethane, melaleuca alternifolia oil, hydroxyethylcellulose, and a pharmaceutically acceptable surfactant;
   (b) applying said oral compound onto said gum tissue; and
   (c) administering an oral probiotic compound, said oral probiotic compound comprising a selection of probiotics; vitamin C; and colostrum.

9. The method of claim 8 wherein said probiotics are selected from the group consisting of lactobacillus acidophilus, lactobacillus plantarum, lactobacillus salivarius, lactobacillus sporogenes, bifidobacterium lon-gum.

10. The method of claim 8 wherein said colostrum is bovine colostrum.

11. The method of claim 8 wherein said administering said oral probiotic compound comprises the step of placing said oral probiotic compound in one's mouth, mixing one's saliva with said oral probiotic compound resulting in a probiotic-mixture, and swishing said probiotic-mixture within one's mouth for between about 10 to 240 seconds.

12. The method of claim 11 further comprising the step of swallowing said probiotic-mixture after completion of said swishing.

13. The method of claim 8 further comprising the step of refraining from rinsing one's mouth and refraining from ingesting any substance for at least about 4 hours after administering said oral probiotic compound.

14. A method of treating gum tissue comprising the steps of:
  (a) providing an oral compound comprising a mixture of water, glycerin, a cranberry source, methysulonylmethane, melaleuca alternifolia oil, hydroxyethylcellulose, and a pharmaceutically acceptable surfactant;
  (b) applying said oral compound onto said gum tissue; and
  (c) engaging in, at most, a daily health regimen of ingesting a systemic immune defense compound one or more times per day, said SID comprising colostrum; beta 1,3 Glucans; fructo-oligosaccharides; amla fruit 4:1; inositol hexaphosphate; minerals; enzymes; a selection of probiotics; and methysulonylmethane.

15. The method of claim 14 wherein said minerals are selected from the group consisting of calcium, zinc, and copper.

16. The method of 15 wherein said calcium, zinc, and copper are chelated.

17. The method of claim 14 wherein said enzymes are selected from the group consisting of amylase, lipase, and cellulase.

18. The method of claim 14 wherein said probiotics are selected from the group consisting of bifidobacterium longum, lactobacillus plantarum bifidobacterium bifidum, lactobacillus casei, and lactobacillus acidophilus.

19. The method of claim 14 wherein said colostrum is bovine colostrum.

20. The method of claim 14 further comprising the step of ingesting said SID at least once at or around morning time and at least once at or around evening time.

21. The method of claim 14 further comprising the step of ingesting said SID at least once approximately after waking from a daily sleep and at least once before retiring for a daily sleep.

22. A method of treating gum tissue comprising the steps of:
  (a) providing an oral compound comprising a mixture of water, glycerin, a cranberry source, methysulonylmethane, melaleuca alternifolia oil, hydroxyethylcellulose, and a pharmaceutically acceptable surfactant;
  (b) applying said oral compound onto said gum tissue; and
  (c) engaging in, at most, a daily health regimen of administering an antimicrobial compound at least once per day, said antimicrobial compound comprising sodium bicarbonate, silicone dioxide, and a cranberry source.

23. The method of claim 22 wherein said cranberry source is selected from the group consisting of cranberry extract and cranberry concentrate powder.

24. The method of claim 22 further comprising the step of administering said antimicrobial compound after each meal or after each brushing of one's teeth or any combination thereof.

25. The method of claim 22 wherein said administering said antimicrobial compound comprises the step of placing said antimicrobial compound in one's mouth, mixing one's saliva with said antimicrobial compound resulting in a antimicrobial-mixture, and swishing said antimicrobial-mixture within one's mouth for between about 10 to 240 seconds.

26. The method of claim 22 further comprising the step of refraining from rinsing one's mouth and refraining from ingesting any substance for between about 30 minutes to about 90 minutes after administering said antimicrobial compound.

27. A method of treating gum tissue comprising the steps of:
  (a) providing an oral compound comprising a mixture of water, glycerin, a cranberry source, methysulonylmethane, melaleuca alternifolia oil, hydroxyethylcellulose, and a pharmaceutically acceptable surfactant;
  (b) applying said oral compound onto said gum tissue; and
  (c) engaging in, at most, a daily health regimen of administering an oral probiotic compound at least once per day, said oral probiotic compound comprising a selection of probiotics; vitamin C; and colostrum.

28. The method of claim 27 wherein said probiotics are selected from the group consisting of lactobacillus acidophilus, lactobacillus plantarum, lactobacillus salivarius, lactobacillus sporogenes, bifidobacterium longum.

29. The method of claim 27 wherein said colostrum is bovine colostrum.

30. The method of claim 27 wherein said administering said oral probiotic compound comprises the step of placing said oral probiotic compound in one's mouth, mixing one's saliva with said oral probiotic compound resulting in a probiotic-mixture, and swishing said probiotic-mixture within one's mouth for between about 10 to 240 seconds.

31. The method of claim 30 further comprising the step of swallowing said probiotic-mixture after completion of said swishing.

32. The method of claim 27 further comprising the step of refraining from rinsing one's mouth and refraining from ingesting any substance for at least about 4 hours after administering said oral probiotic compound.

* * * * *